(12) United States Patent
Arai et al.

(10) Patent No.: US 8,501,977 B2
(45) Date of Patent: Aug. 6, 2013

(54) PLATINUM COMPLEX AND PHARMACEUTICAL COMPOSITION CONTAINING THE SAME

(75) Inventors: Hisae Arai, Kashiwa (JP); Masaji Ohno, Kashiwa (JP); Hisao Kondo, Kashiwa (JP); Ikuko Arai, Kashiwa (JP)

(73) Assignee: Unitech Co., Ltd., Kashiwa-Shi, Chiba (JP)

( * ) Notice: Subject to any disclaimer, the term of this patent is extended or adjusted under 35 U.S.C. 154(b) by 347 days.

(21) Appl. No.: 13/060,906

(22) PCT Filed: Aug. 25, 2009

(86) PCT No.: PCT/JP2009/004077
§ 371 (c)(1),
(2), (4) Date: Feb. 25, 2011

(87) PCT Pub. No.: WO2010/026711
PCT Pub. Date: Mar. 11, 2010

(65) Prior Publication Data
US 2011/0152555 A1 Jun. 23, 2011

(30) Foreign Application Priority Data

Sep. 3, 2008 (JP) .................................. 2008-225698
Jun. 30, 2009 (JP) .................................. 2009-155399

(51) Int. Cl.
*C07F 15/00* (2006.01)
*A61K 31/28* (2006.01)

(52) U.S. Cl.
USPC ............................. 556/40; 556/137; 514/492

(58) Field of Classification Search
USPC ................................... 556/40, 137; 514/492
See application file for complete search history.

(56) References Cited

U.S. PATENT DOCUMENTS

| 4,140,707 | A | 2/1979 | Cleare et al. |
| 5,028,727 | A | 7/1991 | Verbeek et al. |
| 2007/0066850 | A1 | 3/2007 | Hems et al. |

*Primary Examiner* — Porfirio Nazario Gonzalez
(74) *Attorney, Agent, or Firm* — Bacon & Thomas, PLLC

(57) ABSTRACT

A new platinum complex which has strong antitumor activity and has effect with smaller doses and a pharmaceutical composition containing the same are provided. A spiro[4,4]nonane-1,6-diamineplatinum(II) complex which is represented by a following general formula (A). (In the formula, X and Y are same or different, and X and Y represent halogen atoms respectively, or X and Y cooperatively represent a divalent residue which is described by a formula (Z).) The platinum complex has a strong antitumor activity and is efficacious as a therapeutic agent for malignant tumors.

15 Claims, 3 Drawing Sheets

PLATINUM COMPLEX AND PHARMACEUTICAL COMPOSITION CONTAINING THE SAME

TECHNICAL FIELD

This invention relates to a new platinum complex and a pharmaceutical composition as an active ingredient, and particularly to a therapeutic agent for malignant tumors.

BACKGROUND ART

Recently, the malignant tumors come to hold the top of the cause of death. On the other hand, the various kinds of anti-tumor materials are developed. Among these, as to the platinum complex, the antitumor action is acknowledged conventionally, and such as cisplatin [I], carboplatin [II] and oxaliplatin [III] are developed, and used for medical treatment (for example, refer to Non-patent document No. 1 Non-patent document No. 3).

[Chemical Formula 1]

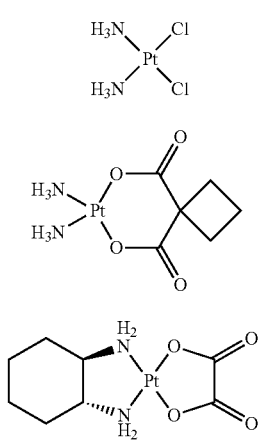

PRIOR ART DOCUMENT

Patent Document

Patent document No. 1: U.S. Pat. No. 4,140,707 (Feb. 20, 1979)

Non-Patent Document

Non-patent document No. 1: Nature, 1969, 222 385-386
Non-patent document No. 2: Canter Treat Reviews, 1985, 12 21-33
Non-patent document No. 3: Cancer Letters, 1985, 27 135-143

SUMMARY OF THE INVENTION

Problem to be Solved by the Invention

However, there were problems that the cisplatin has many side-effects such as nephrotoxicity, hematotoxicity, toxicity for digestive organs, and neurotoxicity. In this situation, the carboplatin was developed as the one which reduced the nephrotoxicity of the cisplatin and increased the water solubility, but the carboplatin was expensive. In addition, the antitumor effect was not necessarily satisfactory.

Although these have the antitumor activity, it is necessary to administer the quantity of predetermined data corresponding to it to work the predefined antitumor activity. Therefore, there is a defect that these have the side-effects.

The object of this invention is to provide the new complex. The new complex is a spiro[4,4]nonane-1,6-diamineplatinum (II) complex, and has the stronger antitumor activity, and has the effect with smaller doses, and thereby the side-effect is reduced relatively.

The abject of this invention is to provide the new complex which has following feature. The new complex is a (cis,cis-spiro[4,4]nonane-1,6-diamine) oxalatoplatinum(II) complex which is described by the following formula (G) especially, and has the strong antitumor activity for a nonsolid tumor like a malignant tumor, particularly the human lymphoma cell. And the side-effect is reduced relatively.

[Chemical Formula 2]

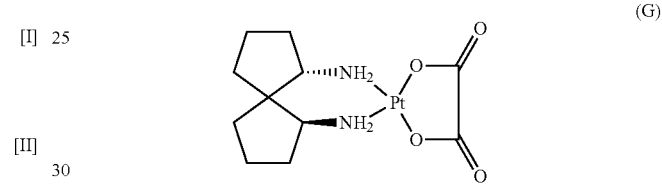

(G)

In addition, because a cis,cis-spiro[4,4]nonane-1,6-diamine exists as the racemate of the optically active substance which has two steric structures, that is, (S,S,S) form and (R,R,R) form, the effect of the platinum complex of these optically active diamine for the malignant tumor is cleared. The aim of this invention is to provide the new complex. The new complex is the optically active (S,S,S) and (R,R,R)-cis, cis-spiro[4,4]nonane-1,6-diamineplatinum (II) complex, and has the stronger antitumor activity, and has the effect with smaller doses, and thereby the side-effect is reduced relatively.

Means for Solving the Problems

For achieving these objects, the therapeutic agent for the malignant tumor of this invention is the new spiro[4,4]nonane-1,6-diamineplatinum(II) complex which is represented by following general formula (A) and assumes the complex the active ingredient.

[Chemical Formula 3]

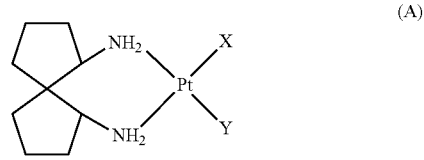

(A)

In the formula, X and Y are same or different, and X and Y represent halogen atoms respectively, or X and Y cooperatively represent the divalent residue which is described by the formula (Z).

[Chemical Formula 4]

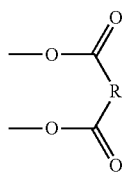
(Z)

In the formula, R represents the single bond or represents the straight-chain or branched-chain divalent hydrocarbon residue whose number of carbon atom is 1-6. The hydrocarbon residue may have the unsaturated bond, and the hydrocarbon residue may form the Spiro structure.

This invention is a (S,S,S)-cis,cis-spiro[4,4]nonane-1,6-diamineplatinum(II) complex which is represented in the general formula (B) of the following formula.

[Chemical Formula 5]

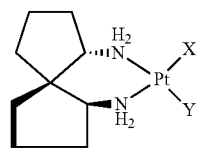
(B)

In the formula, X and Y are same or different, and X and Y represent halogen atoms respectively, or X and Y cooperatively represent the divalent residue which is represented by the formula (Z).

[Chemical Formula 6]

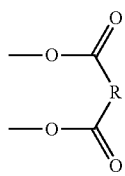
(Z)

In the formula, R represents the single bond or represents the straight-chain or branched-chain divalent hydrocarbon residue whose number of carbon atom is 1-6. The hydrocarbon residue may have the unsaturated bond, and the hydrocarbon residue may form the spiro structure.

This invention is a (R,R,R)-cis,cis-spiro[4, 4]nanane-1,6 diamineplatinum(II) complex which is represented in the general formula (C) of the following formula.

[Chemical Formula 7]

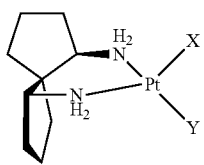
(C)

In the formula, X and Y are same or different, and X and Y represent halogen atoms respectively, or X and Y cooperatively represent the divalent residue which is represented by the formula (Z).

[Chemical Formula 8]

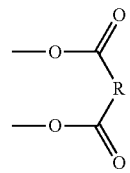
(Z)

In the formula, R represents the single bond or represents the straight-chain or branched-chain divalent hydrocarbon residue whose number of carbon atom is 1-6. The hydrocarbon residue may have the unsaturated bond, and the hydrocarbon residue may form the spiro structure.

This invention is a (spiro[4,4]nonane-1,6-diamine)dicarboxylatoplatinum(II) complex which is represented in the general formula (D) of the following formula.

[Chemical Formula 9]

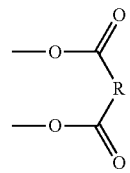
(D)

In the above-mentioned formula, R represents the single bond or represents the straight-chain or branched-chain divalent hydrocarbon residue whose number of carbon atom is 1-6. The hydrocarbon residue may have the unsaturated bond, and the hydrocarbon residue may form the spiro structure.

This invention is a ((S,S,S)-cis,cis-spiro[4,4]nonane-1,6-diamine)dicarboxylatoplatinum(II) complex which is represented in the general formula (E) of the following formula.

[Chemical Formula 10]

(E)

In the formula, R represents the single bond or represents the straight-chain or branched-chain divalent hydrocarbon residue whose number of carbon atom is 1-6. The hydrocarbon residue may have the unsaturated bond, and the hydrocarbon residue may form the spiro structure.

This invention is a ((R,R,R)-cis,cis-spiro[4,4]nonane-1,6-diamine)dicarboxylatoplatinum(II) complex which is represented in the general formula (F) of the following formula.

[Chemical Formula 11]

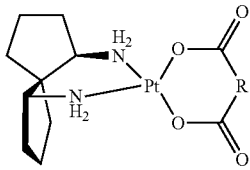

(F)

In the formula, R represents the single bond or represents the straight-chain or branched-chain divalent hydrocarbon residue whose number of carbon atom is 1-6. The hydrocarbon residue may have the unsaturated bond, and the hydrocarbon residue may form the spiro structure.

This invention is a (cis,cis-spiro[4,4]nonane-1,6-diamine)oxalatoplatinum(II) complex which is represented in the following formula (G).

[Chemical Formula 12]

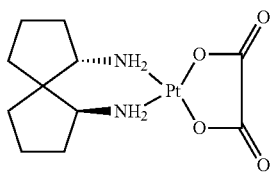

(G)

This invention is a ((S,S,S)-cis,cis-spiro[4,4]nonane-1,6-diamine)oxalatoplatinum(II) complex which is represented in the following formula (H).

[Chemical Formula 13]

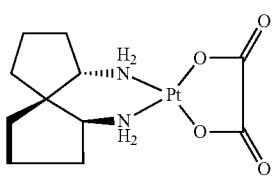

(H)

This invention is a ((R,R,R)-cis,cis-spiro[4,4]nonane-1,6-diamine)oxalatoplatinum(II) complex which is represented in the following formula (J).

[Chemical Formula 14]

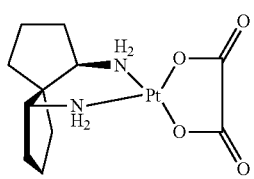

(J)

This invention is a (cis,cis-spiro[4,4]nonane-1,6-diamine)cyclobutanedicarboxylatoplatinum(II) complex which is represented in the following formula (K).

[Chemical Formula 15]

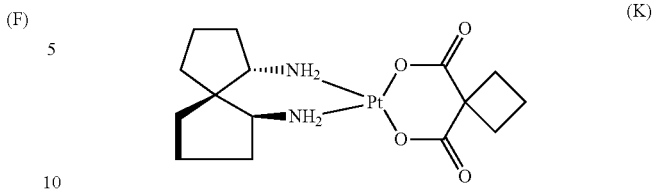

(K)

This invention is a (cis,trans-spiro[4,4]nonane-1,6-diamine)cyclobutanedicarboxylatoplatinum(II) complex which is represented in the following formula (L).

[Chemical Formula 16]

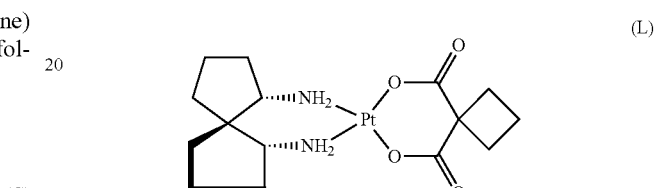

(L)

This invention is a pharmaceutical composition that the platinum complex of the above-mentioned each formula is contained as the active ingredient.

This invention is the therapeutic agent for the malignant tumor that the platinum complex of each of the foregoing formulas is contained as the active ingredient.

This invention is the foregoing pharmaceutical composition which is the therapeutic agent for the malignant tumor.

This invention is the foregoing pharmaceutical composition which is the therapeutic agent for a nonsolid malignant tumor.

EFFECT OF THE INVENTION

The new platinum complex of this invention has the strong antitumor activity for the nonsolid tumor such as the malignant tumor, especially human lymphoma cell, and has the effect compared with the conventional therapeutic agent for the malignant tumor of the platinum complex with smaller doses. Therefore, the side-effect is reduced relatively.

DETAILED DESCRIPTION OF THE PREFERRED EMBODIMENTS OF THE INVENTION

Figure 1:
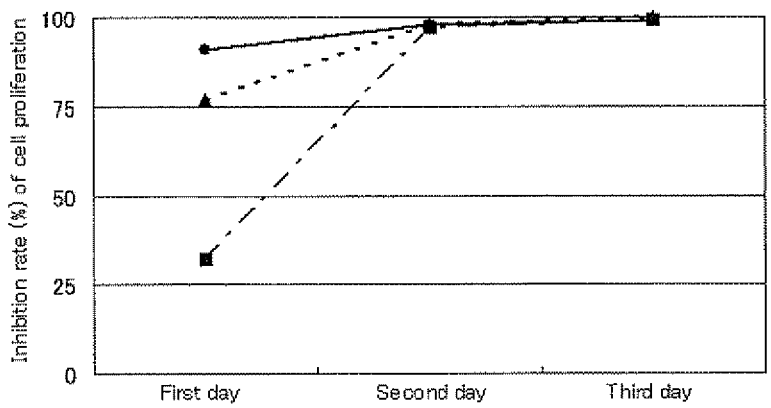
FIG. 1 The graph representing the inhibition rate (%) of the cell proliferation when making the (compound 1) of this invention act on the cancer cell and the normal cell.
Figure 1:
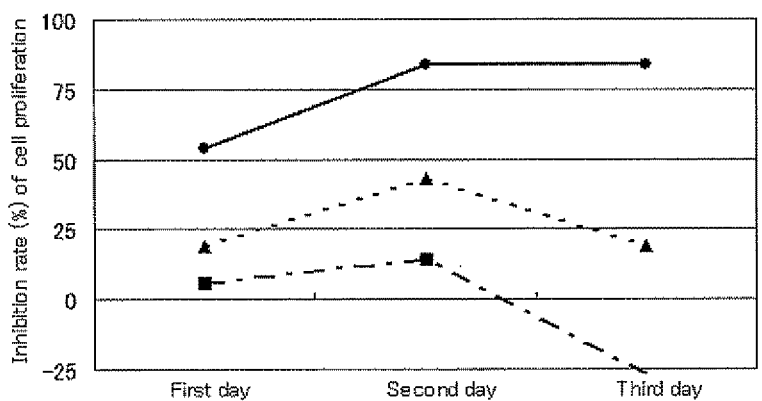
Figure 1:
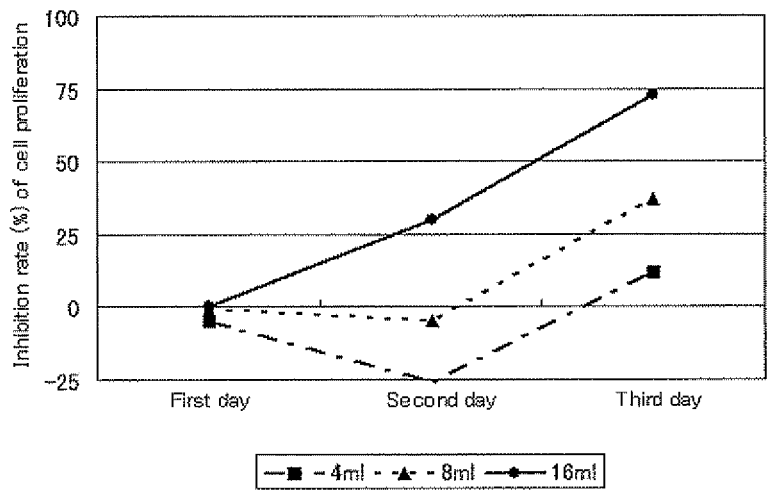

Hereinafter, the platinum complex of this invention and the therapeutic agent for the malignant tumor containing it are explained in connection with the embodiments.

As to the platinum complex of this invention, in the spiro [4,4]nonane-1,6-diamine, three stereo isomers of cis,cis-form, cis, trans-form and trans, trans-form exist on stereochemistry. However, as to the trans, trans-form, because it is impossible to form the complex with the platinum in the inside of the molecule sterically, the cis,cis-form and the cis,trans-form are preferable.

When X and Y represent the halogen atoms, it is preferable that X and Y are same halogen atoms, and especially, it is preferable that X and Y are chlorine atoms together.

Meanwhile, the compound that X and Y are described cooperatively in the formula (Z) originates from the dicarboxylic acid which forms the complex with the platinum.

In the case that R is the single bond, the dicarboxylic acid is the oxalic acid, and in the cage that R is the hydrocarbon residue whose number of carbon atom is 1-6, for example, respectively, when R is 1, the dicarboxylic acid is the malonic acid, and when R is 2, the dicarboxylic acid is the succinic acid, and when R is 3 of the straight-chain, the dicarboxylic acid is the glutaric acid.

In the cage that the hydrocarbon residue of R has the unsaturated bond, for example, the dicarboxylic acid that R has the number of carbon atom of 2 is the maleic acid.

In the cage that the hydrocarbon residue of R has the spiro structure, as the dicarboxylic acid which is the cyclic hydrocarbon whose number of carbon atom is 3-6, and which has two bonds in the same carbon atom, for example, a cyclopropane-1,1-dicarboxylic acid and a cyclobutane-1,1-dicarboxylic acid are enumerated.

As the dicarboxylic acid which forms the salt with the platinum, the oxalic acid that R is the single bond and a cyclobutanedicarboxylic acid that number of carbon atom of R is 4 are preferable.

The compound containing the stereo isomer of this invention is synthesized by the method represented by the reaction formulas (i) and (ii) which are described in the following general formula.

[Chemical Formula 17]

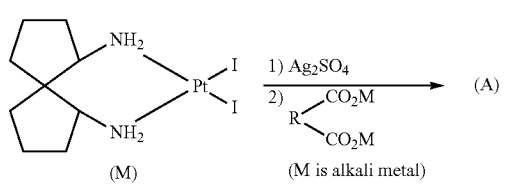

(M)    (M is alkali metal)

[Chemical Formula 18]

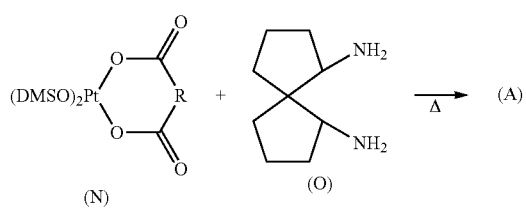

The compounds (M), (N) are obtained easily by applying the heretofore known method, for example the methods which are described in J. Med. Chem., 1997, 40, 112-116, and J. Inorg. Biochem., 1996, 61, 291-310. DMSO is the abbreviation of dimethylsulfoxide.

[Chemical Formula 19]

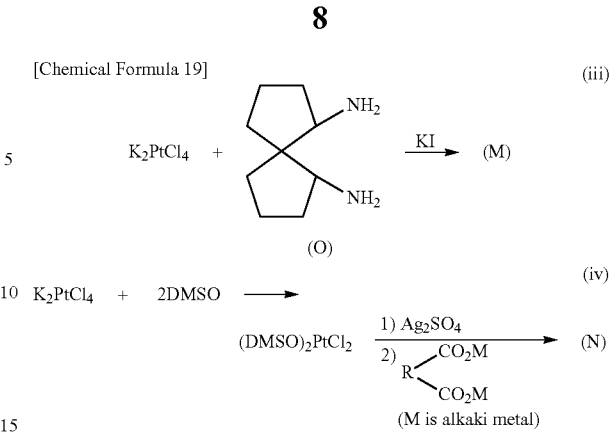

The compound of the formula (M) can be the objective compound (A) of this invention in itself.

The compound which is the halogen atom except iodine in the formula (M) is manufactured as well as (M), or can be also manufactured according to the ordinary method by displacing the iodine atom of the compound of (M) to the other halogen atom.

As to the compound of (M), in the spiro[4,4]nonane-1,6-diamine which is used, three stereo isomers of cis,cis-form, cis, trans-form and trans,trans-form exist on stereochemistry. However, in the trans,trans-form, it is impossible to form the complex in the inside of the molecule on stereochemistry. Therefore, the cis,cis-form and the cis,trans-form become two steric structure isomers.

As the alkali metal salt of the dicarboxylate which is used in the reaction formula (i), Na salt and K salt are preferable, and it is preferable to use the equivalent. As to the compound (N) and (O) in the reaction formula (ii), it is preferable to use the equivalent.

The spiro[4,4]nonane-1,6-diamine which is described by the formula (O) which is another material can be synthesized by the heretofore known method (A.C.C. Chan et al., Tetrahedron. Lett., 2004, 45, 7379), for example, the method which is described by the reaction formula (V). That is, it is possible to synthesize by the three steps from the spiro[4,4]nonane-1,6-dial (P).

[Chemical Formula 20]

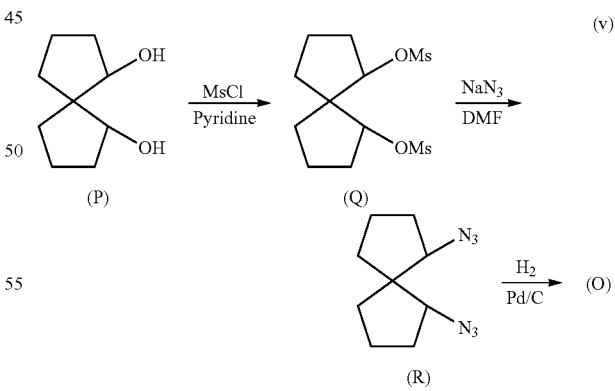

Here, MsCl represents the methanesulfonylchloride ($CH_3SO_2Cl$). In the compound (O), three structural isomers, that is, the cis,cis-form, the cis,trans-form and the trans,trans-form exist. However, among these, the two of the cis,cis-form and the cis,trans-form form the complex with the platinum in the inside of the molecule. As these are described by the reaction formula (iv) and (v), the cis,cis [4,4]nonane-1,6- diamine (c,c-O) can be synthesized from the trans, trans-spiro[4,4]nonane-1,6-diol (t, t-P) which corresponds stereoselectively, and the cis,trans-spiro[4,4]nonane-1,6-diamine (c,t-O) can be synthesized from the cis,trans-spiro[4,4]nonane-1,6-diol (t,c-P).

[Chemical Formula 21]

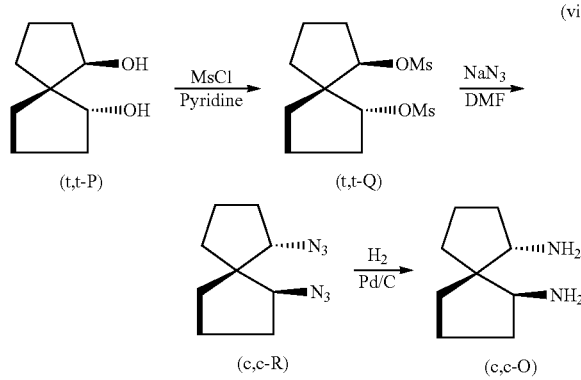

(vi)

[Chemical Formula 22]

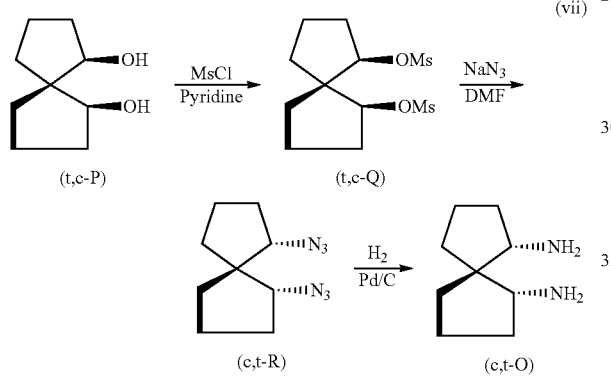

(vii)

The trans,trans-spiro[4, 4]nonane-1,6-diol (t,t-P) and the trans, cis-spiro[4,4]nonane-1,6-diol (t,c-O) are obtained by the heretofore known method (J. A. Nieman, B. A. Keay, Synthetic Comm., 1999, 29, 3929), for example, are obtained by the method which reduces the spiro[4,4]nonane-1,6-dione (S) by the appropriate reducing agent, for example, the metal hydride such as Na[(CH$_3$OCH$_2$CH$_2$O)$_2$AlH$_2$].

[Chemical Formula 23]

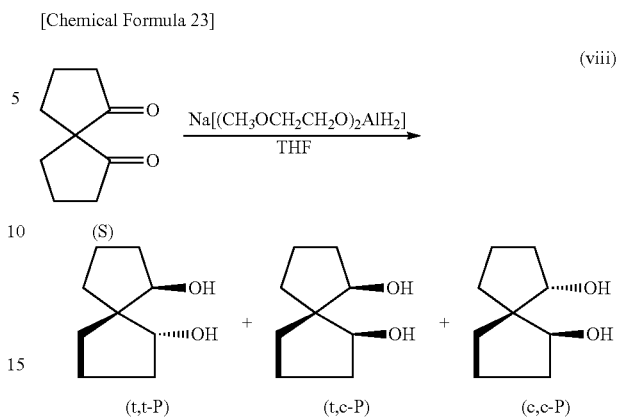

(viii)

Although the three isomeric mixtures are usually obtained, these can be separated by the heretofore known method, for example, the method of D. J. Cram et al. J. Am. Chem. Soc., 1959, 81 2729.

The spiro[4,4]nonane-1,6-dione (S) can be synthesized by the heretofore known method, for example, the method of J. A. Nieman, B. A. Keay, Synthetic Comm., 1999, 29, 3929.

[Chemical Formula 24]

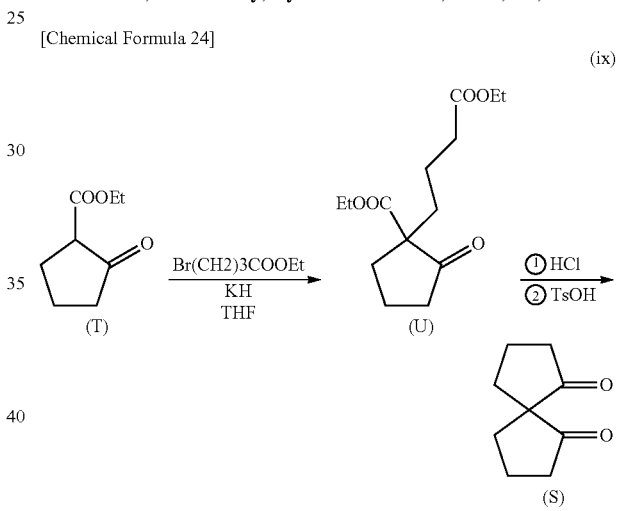

(ix)

When using the diamine (c,c-O), (c,t-O) which are synthesized here to the reaction formulas (i) and (ii), the platinum complex which corresponds respectively can be synthesized.

[Chemical Formula 25]

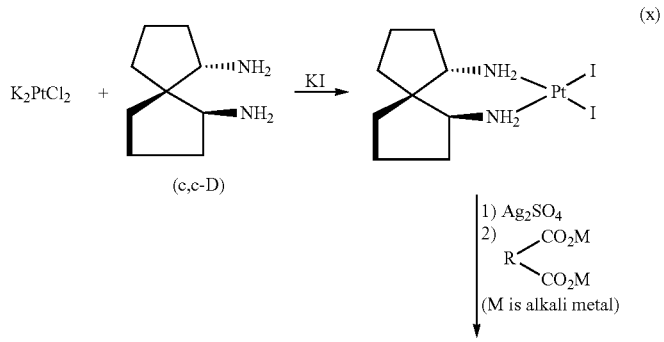

(x)

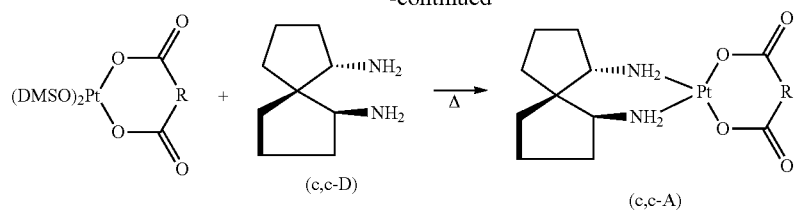

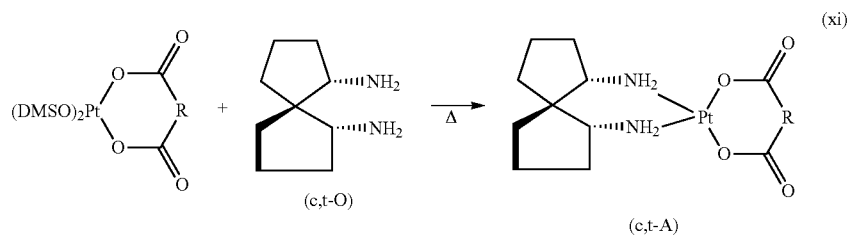

Besides, the compound containing the optical isomer of this invention is synthesized by the method which is represented in the reaction formulas (I) and (II) which are represented in the following general formulas.

method which is described in J. Med. Chem., 1997, 40, 112-116, J. Inorg. Biochem., 1993, 50, 79-87 and J. Inorg. Biochem., 1996, 61, 291-310. DMSO is the dimethylsulfoxicle.

[Chemical Formula 27]

[Chemical Formula 29]

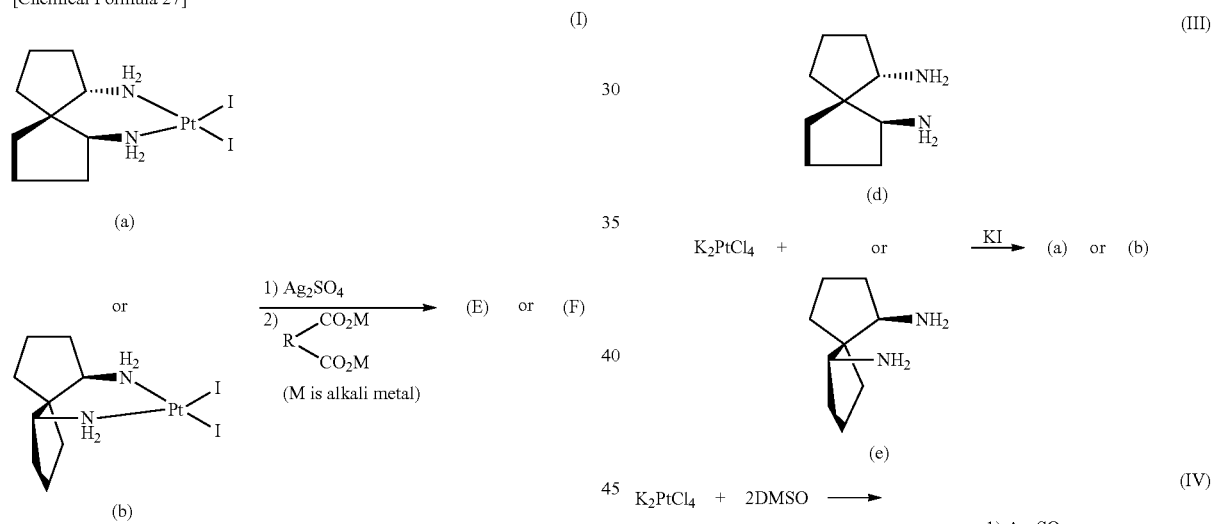

[Chemical Formula 28]

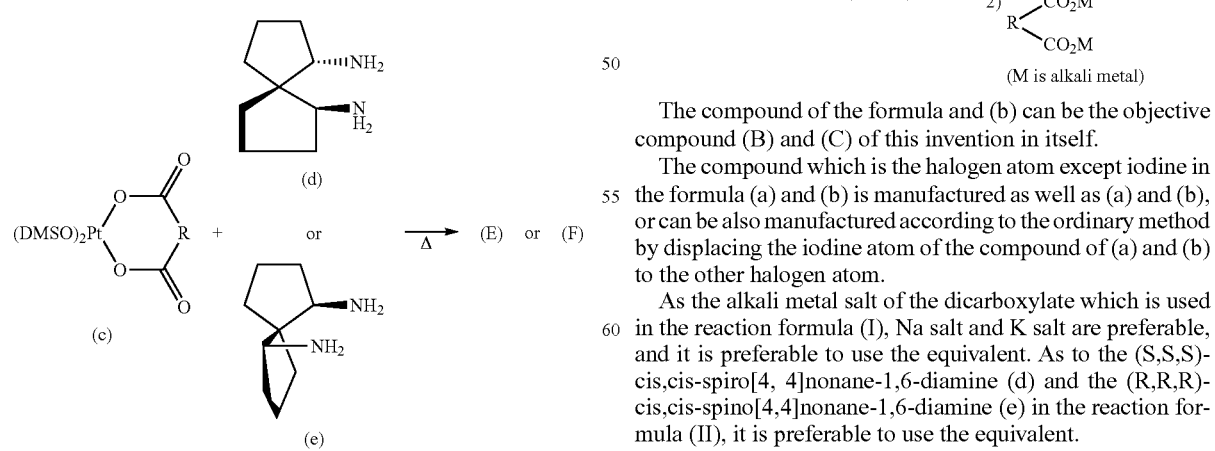

The compound (a), (b) and (c) are obtained easily by the heretofore known method, for example, by applying the The compound of the formula and (b) can be the objective compound (B) and (C) of this invention in itself.

The compound which is the halogen atom except iodine in the formula (a) and (b) is manufactured as well as (a) and (b), or can be also manufactured according to the ordinary method by displacing the iodine atom of the compound of (a) and (b) to the other halogen atom.

As the alkali metal salt of the dicarboxylate which is used in the reaction formula (I), Na salt and K salt are preferable, and it is preferable to use the equivalent. As to the (S,S,S)-cis,cis-spiro[4, 4]nonane-1,6-diamine (d) and the (R,R,R)-cis,cis-spino[4,4]nonane-1,6-diamine (e) in the reaction formula (II), it is preferable to use the equivalent.

The (S,S,S)-cis,cis-spiro[4,4]nonane-1,6-diamine and the (R,R,R)-cis,cis-spiro[4,4]nonane-1,6-diamine which are represented by the formulas (d) and (e) can be synthesized by the heretofore known method (A.C.C. Chan et al. Tetrahedron. Lett., 2004, 45, 7379), for example, the method which is represented in the reaction formula (V).

[Chemical Formula 30]

(V)

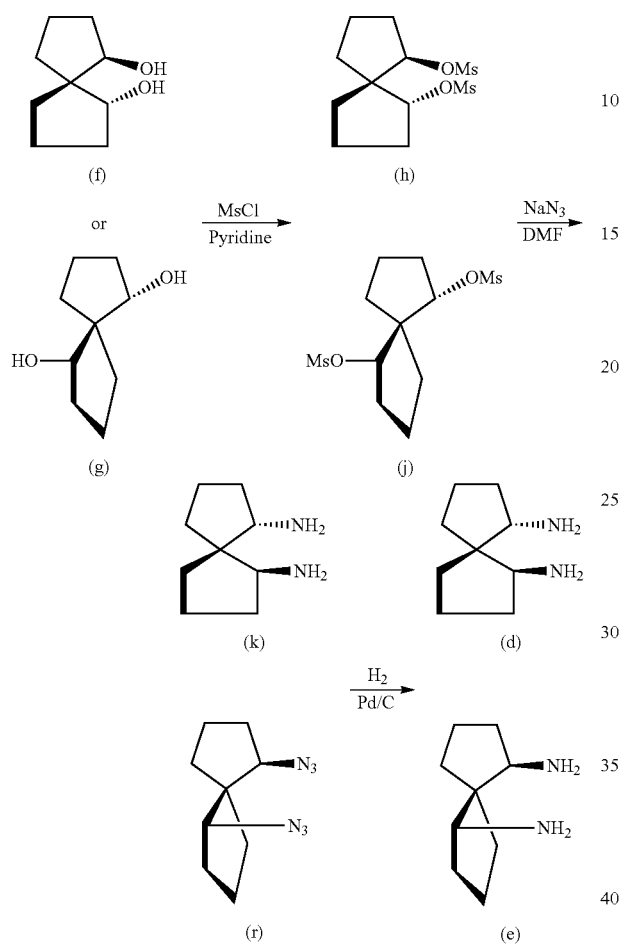

Namely, it is possible to synthesize by the three steps from the (R,S,R)-trans,trans-spiro[4,4]nonane-1,6-diol (f) and the (S,R,S)-trans,trans-spiro[4,4]nonane-1,6-diol (g) which correspond and are optically-active.

Here, MsCl represents the methanesulfonylchloride (CH$_3$SO$_2$Cl). The (R,S,R)-trans,trans-spiro[4,4]nonane-1,6-diol (f) and the (S,R,S)-trans,trans-spiro[4,4]nonane-1,6-diol (g) can be synthesized by the heretofore known method (A.C.C. Chan et al. Tetrahedron. Lett., 2004, 45, 7379), that is, the method which reduces the spiro[4,4]nonane-1,6-dione (m) by borane by using known and optically-active (S)-CBS (n) or (R)-CBS(o) as the catalyst. When the (S)-CBS catalyst is used, the (R,S,R)-trans,trans-spino[4,4]nonane-1,6-diol (f) is obtained, and when the (R)-CBS catalyst is used, the (S,R, S)-trans,trans-spiro[4,4]nonane-1,6-diol (g) is obtained.

[Chemical Formula 31]

(VI)

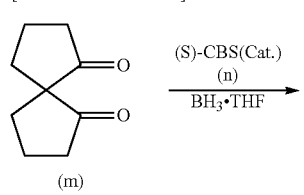

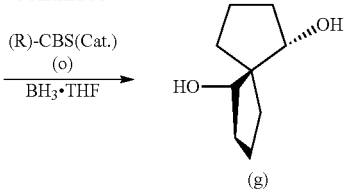

The (S)-CBS catalyst (n) and the (R)-CBS catalyst (o) can be synthesized by the heretofore known method (E. J. Corey, R. K. Bakshi, S. Shibata, J. Am. Chem. Soc., 1987, 109, 5551) by the reaction formula (VII) of following formula.

[Chemical Formula 32]

(VII)

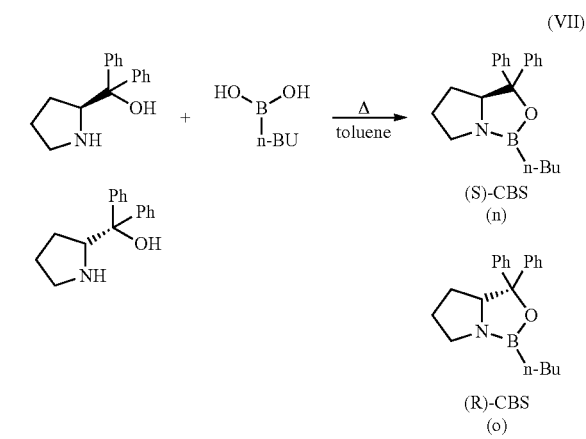

The spiro[4,4]nonane-1,6-dione (m) can be synthesized by the heretofore known method, for example, the method of J. A. Nieman, B. A. Keay, Synthetic Comm., 1999, 29, 3929.

[Chemical Formula 33]

(VIII)

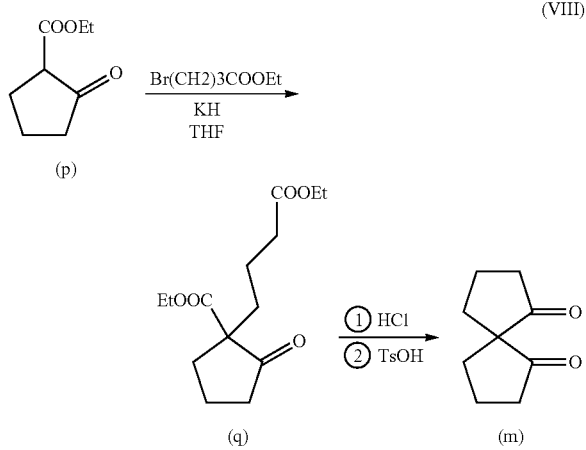

When using the optically-active diamine (d) and which are synthesized here to the reaction formulas (I) and (II), the platinum complexes which correspond respectively can be synthesized.

Although there is the case that this complex contains water as an aqueous complex, the aqueous body is also contained in this invention.

When the pharmaceutical composition which contains the efficacious dose of the platinum complex of this invention is administered in the clinical practice, it is performed by the oral administration or the parenteral administration. The formulation includes such as tablet, sugar-coated tablet, ball, capsule, powdered medicine, lozenge, liquid medicine, suppository, injectable solution, and these are manufactured by blending the excipients which are allowable as medicine. It is preferable that the pharmaceutical composition of this invention is adjusted as the parenteral formulation. As the excipient, the following one can be exemplified. These are such as lactose, sucrose, glucose, sorbitol, mannitol, potato starch, amylopectin, other various starches, cellulose derivative (for example, carboxymethyl cellulose, hydroxyethyl cellulose), gelatin, calcium stearate, magnesium stearate, polyvinyl alcohol, polyethylene glycol wax, gum arabic, talc, titanium dioxide, vegetable oil such as olive oil, peanut oil or sesame oil, paraffin oil, neutral fat base, ethanol, propylene glycol, saline, sterilized water, glycerin, coloring agent, seasoned formulation, thickener, stabilizer, isotonic agent, buffering agent, and other excipients which are allowable as medicine.

The therapeutic agent of this invention can contain the platinum complex of this invention of 0.001-85% by weight, and preferably, can contain the platinum complex of 0.005-60% by weight.

The dose of the therapeutic agent of this invention is mainly influenced by the symptom. However, it is 0.005-200 mg per an adult weight per a day, and preferably, it is 0.01-50 mg.

The embodiments are enumerated as follows, and this invention is explained more concretely.

Embodiment 1

The potassium tetrachloroplatinum(II) ($K_2PtCl_4$) of 7.47 g (18 mmol) was put in the round bottom flask of 300 ml, and was dissolved in the water of 145 ml, and the solution that the potassium iodide (KI) of 29.9 g was dissolved in the water of 40 ml was added into this, and these were stirred for one hour at roan temperature. Next, the cis,cis-spino[4,4]nonane-1,6-diamine of 2.81 g (18 mmol) was added, and these were stirred for 22 hours at roan temperature. The filtration was performed, and the filtered one was washed by water, then by ethanol, and further by diethyl ether, and was dried. The (cis,cis-spino[4,4]nonane-1,6-diamine) diiodeplatinum (II) complex of 8.47 g was obtained. The yield was 87%.

The distilled water of 150 ml and the acetone of 15 ml were pit in the round bottom flask of 20 ml, and additionally the (cis,cis-sprio[4,4]nonane-1,6-diamine)diiodeplatinum(II) complex of 3 g (4.97 mmol) was added, finally the silver sulfate of 1.47 g (4.72 mmol) was added, and these were stirred for 28 hours at room temperature under the dark room. The non-dissolved material was filtered. The filtrate was concentrated till about 20 ml under the reduced pressure. Next, the solution that the oxalic acid of 402 mg (4.47 mmol) was dissolved in the 1 N sodium hydroxide water solution of 8.9 ml (8.9 mmol) was added, and these were stirred for one hour at room temperature under the dark room. The filtration was performed after cooling till 4 degrees centigrade The filtered one was washed by cold water, then was washed by acetone, and was dried.
The (cis,cis-spiro[4,4]nonane-1,6-diamine) oxalatoplatinum (II) complex (compound 1) of 1.28 g was obtained. The yield was 59%.
Elementary analysis (as $C_{11}H_{18}N_2O_4Pt$)
Calculated value (%) C: 30.21 H: 4.15 N: 6.41 Pt: 44.60
Measured value (%) C: 29.11 H: 4.22 N: 6.09 Pt: 44.57
IR (KEBr) $cm^{-1}$: 3203, 3115, 1693, 1672, 1367

$^1$H-NMR (500 Hz, DMSO-d6) δ: 1.35 (t, J=9.5 Hz, 2 H), 1.45-1.53 (m, 2 H), 1.55-1.61 (m, 2 H), 1.65-1.69 (m, 4 H), 1.82-1.89 (m, 2 H), 2.91-2.95 (q, J=5.8 Hz, 2 H), 5.04 (t, J=11.6 Hz, 2 H), 5.87 (d, J=10.5 Hz, 2 H)
$^{13}$C-NMR (125 MHZ, DMSO-d6) δ: 20.6, 32.7, 35.2, 56.3, 60.4, 166.2
MS (FAB): m/z 438 (M+H$^+$)

From the above results, it was identified that this compound had the chemical structure which was represented by the (compound 1).

[Chemical Formula 34]

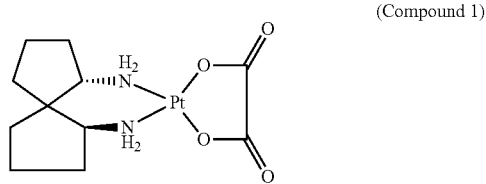

(Compound 1)

Embodiment 2

The potassium tetrachloroplatinum(II) ($K_2PtCl_4$) of 6.26 g (15.1 mmol) was put in the round bottom flask of 50 ml, and was dissolved in the water of 100 ml, subsequently the dimethylsulfoxide (DMSO) of 3.34 g (42.8 mmol) was added, and these were put statically for two days. The crystal which precipitated was filtered, then was washed by cold water, further was washed by acetone, and was dried. $(DMSO)_2PtCl_2$ which is the DMSO complex of 5.44 g was obtained. The yield was 84.3%.

The $(DMSO)_2PtCl_2$ of 2.60 g (6.1 mmol) which is the bis(dimethylsufoxide)dichloroplatinum complex which was obtained here was put in the round bottom flask of 200 ml, subsequently the water of 110 ml was added, further the silver sulfate ($Ag_2SO_4$) of 1.86 g (6.0 mmol) was added, and these were stirred for 19 hours at room temperature in the dark place. Celite as the filter aid was used and the filtration was performed. The water solution that the oxalic acid of 554 mg was dissolved in the 1N sodium hydroxide solution of 12.6 ml was added in the filtrate, and these were stirred for four hours at roan temperature. The filtration was performed, and the filtered one was washed by cold water, then was washed by acetone, and was dried, The $(DMSO)_2Pt$ (oxalate) which is the bis(dimethylsufoxide)oxalatoplatinum complex of 2.12 g was obtained. The yield was 79.1%.

The cis,cis-spiro[4,4]nonane-1,6-diamine of 78 mg (0.5 mmol) was dissolved in the water of 10 ml, and the filtration was performed. The $(DMSO)_2Pt(oxalate)$ of 220 mg (0.5 mmol) which was obtained previously was added into the filtrate, and these were heated and stirred for 1.5 hours at 90 degrees centigrade. The white solid appeared. The filtration was performed after cooling till 4 degrees centigrade. The filtered one was washed by cold water, then was washed by acetone, and was dried. The (cis,cis-spiro[4,4]nonane-1,6-diamine) oxalatoplatinum (II) complex (compound 1) of 145 mg was obtained. The yield was 66%. The IR of this substance corresponded to the one which was obtained in the embodiment 1 perfectly.

Embodiment 3

The potassium tetrachloroplatinum (II) ($K_2PtCl_4$) of 5.81 g (14 mmol) was put in the round bottom flask of 300 ml, and was dissolved in the water of 112 ml, and the solution that the potassium iodide (KI) of 23.26 g was dissolved in the water of 31 ml was added into this, and these were stirred for one hour at room temperature. Next, the (S,S,S)-cis,cis-spiro[4,4] nonane-1,6-diamine of 2.19 g (14 mmol) was added, and these were stirred for 22 hours at room temperature. The filtration was performed, and the filtered one was washed by water, then was washed by ethanol, and further was washed by diethyl ether, and was dried. The ((S,S,S)-cis,cis-spiro[4, 4]nonane-1,6-diamine) diiodeplatinum (II) complex of 7.17 g was obtained. The yield was 85%.

The distilled water of 150 ml and the acetone of 15 ml were put in the round bottom flask of 200 ml, and the ((S,S,S)-cis,cis-spiro[4,4]nonane-1,6-diamine) diiodeplatinum (II) complex of 3 g (4.97 mmol) was added, finally the silver sulfate of 1.47 g (4.72 mmol) was added, and these were stirred for 71 hours at room temperature under the dark room. The non-dissolved material was filtered. The filtrate was concentrated till about 20 ml under the reduced pressure. Next, the solution that the oxalic acid of 402 mg (4.47 mmol) was dissolved in the 1N sodium hydroxide water solution of 8.9 ml (8.9 mmol) was added, and these were stirred for one hour at room temperature under the dark room. The filtration was performed after cooling till 4 degrees centigrade. The filtered one was washed by cold water, then was washed by acetone, and was dried.

The ((S,S,S)cis,cis-spiro[4,4]nonane-1,6-diamine) oxalatoplatinum complex (compound 2) of 1.02 g was obtained. The yield was 47%.

IR(KBr) cm$^{-1}$: 3200, 3111, 1701, 1670, 1375

The result of IR measurement corresponded to the compound 1 of the embodiment 1, and it was identified as the compound 2.

[Chemical Formula 35]

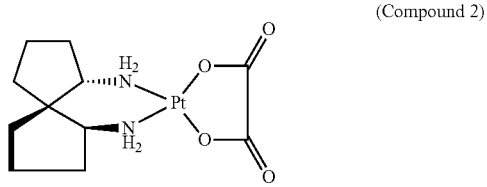

(Compound 2)

Embodiment 4

The potassium tetrachloroplatinum(II) (K$_2$PtCl$_4$) of 5.84 g (14 mmol) was put in the round bottom flask of 300 ml, and was dissolved in the water of 114 ml, and the solution that the potassium iodide (KI) of 23.41 g was dissolved in the water of 31 ml was added into this, and these were stirred for one hour at room temperature. Next, the (R,R,R)-cis,cis-spiro[4,4] nonane-1,6-diamine of 2.20 g (14 mmol) was added, and these were stirred for 22 hours at roan temperature. The filtration was performed, and the filtered one was washed by water, then was washed by ethanol, and further was washed by diethyl ether, and was dried. The ((R,R,R)-cis,cis-spiro[4, 4]nonane-1,6-diamine) diiodeplatinum(II) complex of 7.34 g was obtained. The yield was 87%.

The distilled water of 150 ml and the acetone of 15 ml were put in the round bottom flask of 200 ml, and the ((R,R,R)-cis,cis-spiro[4,4]nonane-1,6-diamine)diiodeplatinum(II) complex of 3 g (4.97 mmol) was added, finally the silver sill fate of 1.47 g (4.72 mmol) was added, and these were stirred for 28 hours at room temperature under the dark room. The non-dissolved material was filtered. The filtrate was concentrated till about 20 ml under the reduced pressure. Next, the solution that the oxalic acid of 402 mg (4.47 mmol) was dissolved in the 1N sodium hydroxide water solution of 8.9 ml (8.9 mmol) was added, and these were stirred for one hour at room temperature under the dark room. The filtration was performed after cooling till 4 degrees centigrade. The filtered one was washed by cold water, then was washed by acetone, and was dried.

The ((R,R,R)cis,cis-Spiro[4,4]nonane-1,6-diamine) oxalatoplatinum (II) complex (compound 3) of 1.15 g was obtained. The yield was 53%.

IR (KBr) cm$^{-1}$: 3202, 3111, 1697, 1674, 1377

The result of IR measurement corresponded to the compound 1 of the embodiment 1, and it was identified as the compound 3.

[Chemical Formula 36]

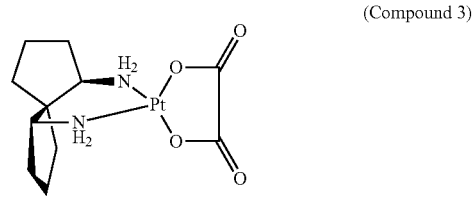

(Compound 3)

Embodiment 5

The (DMSO)$_2$PtCl$_2$ of 3.77 g (8.93 mmol) which is the bis(dimethylsulfoxide)dichloroplatinum complex which was obtained in the embodiment 2 was put in the round bottom flask of 200 ml, subsequently the water of 100 ml was added. Additionally, the cyclobutanedicarboxylic acid (CBDCA) of 1.22 g, and the 0.5 N sodium hydroxide water solution of 34 ml, subsequently the silver nitrate (AgNO$_3$) of 2.89 g (17 mmol) were added, and these were stirred for 46 hours at room temperature in the dark place. The filtration was performed, and the filtered one was washed by cold water, then was washed by acetone, and was dried. The (DMSO)$_2$Pt (CBDCA) which is the bis(dimethylsulfoxide)cyclobutane-1,1-dicarboxylatoplatinum(II) complex of 2.55 g was obtained. The yield was 57.9%.

The cis,cis-spiro[4,4]nonane-1,6-diamine of 760 mg (4.86 mmol) was dissolved in the water of 10 ml, and the filtration was performed. The filtrate was added to the round bottom flask of 30 ml, the (DMSO)$_2$Pt(CBDCA) which is the bis (dimethylsulfoxide) cyclobutane-1,1-dicarboxylatoplatinum (II) complex of 2.4 g (4.86 mmol) which was obtained above was added into the filtrate, and these were heated and stirred for 1.5 hours at 90 degrees centigrade. The white solid appeared after about 30 minutes. The filtration was performed after cooling at 4 degrees centigrade. The filtered one was washed by cold water, then was washed by acetone, and was dried.

The objective (cis,cis-spiro[4,4]nonane-1,6-diamine)cyclobutane-1,1-dicarboxylatoplatinum(II) complex (compound 4) of 1.44 g was obtained. The yield was 60%.

Elementary analysis (as C$_{15}$H$_{24}$N$_2$O$_4$Pt.H$_2$O)

| | | | | |
|---|---|---|---|---|
| Calculated value (%) | C: 35.36 | H: 5.14 | N: 5.50 | Pt: 38.29 |
| Measured value (%) | C: 34.63 | H: 5.24 | N: 5.30 | Pt: 37.99 |

IR(KBr) cm⁻¹: 3207, 3098, 1661, 1672, 1373

¹H-NMR (500 Hz, DMF-d7) δ: 1.49-1.53 (m, 2 H), 1.58-1.65 (m, 2 H), 1.70 (quint, J=7.9 Hz, 2 H), 1.75-1.80 (m, 2 H), 1.82-1.89 (m, 2 H), 1.91-1.97 (m, 2 H), 2.00-2.07 (m, 2 H), 3.17-3.20 (m, 2 H), 5.09 (t, J=11.3 Hz, 2 H), 5.64 (d, J=11.0 Hz, 2 H) ¹³C-NMR (125 MHZ, DMF-d7) δ: 15.8, 21.2, 31.3, 33.6, 6.3, 56.7, 57.4, 61.7, 178.6 MS (FAB): m/z 492 (M+H⁺)

From the above results, it was identified that this compound had the chemical structure which was represented by the (compound 4).

[Chemical Formula 37]

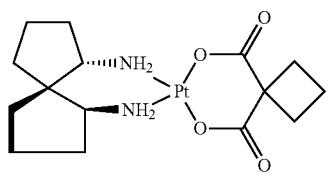

(Compound 4)

Embodiment 6

The cis,trans-spiro[4,4]nonane-1,6-diamine of 997 mg (6.38 mmol) was dissolved in the water of 100 ml, and the filtration was performed. The filtrate was added to the round bottom flask of 200 ml, subsequently the (DMSO)₂Pt (CB-DCA) which is the bis (dimethylsulfoxide) cyclobutane-1,1-dicarboxylatoplatinurn(II) complex of 3.15 g (6.38 mmol) which was obtained in the embodiment 5 was added into the filtrate, and after these were stirred for 26 hours at room temperature, these were heated and stirred for 2.5 hours at 90 degrees centigrade. It was recognized that the white solid appeared after about 1 hour. The filtration was performed after cooling at 4 degrees centigrade. The filtered one was washed by cold water, then was washed by acetone, and was dried. The (cis,trans-spiro[4,4]nonane-1,6-diamine) cyclobutane-1,1-dicarboxylatoplatinum(II) complex (compound 5) of 1.12 g was obtained. The yield was 36%.

Elementary analysis (as C₁₅H₂₄N₂O₄Pt)

| Calculated value (%) | C: 36.66 | H: 4.92 | N: 5.70 | Pt: 39.70 |
| Measured value (%) | C: 36.56 | H: 4.88 | N: 5.57 | Pt: 39.91 |

IR(KBr) cm⁻¹: 3209, 3115, 1651, 1614, 1373

¹H-NMR (500 Hz, DMSO-d6) δ: 1.13-1.17 (m, 1H), 1.24-1.29 (m, 1H), 1.33-1.52 (m, 2 H), 1.59-1.72 (m, 2H), 1.79-1.82 (m, 2 H), 1.87-1.94 (m, 1H), 1.98-2.09 (m, 3 H), 2.53-2.60 (m, 2 H), 2.68 (q, J=9.2 Hz, 1H), 2.78-2.80 (m, 1H), 2.87-2.92 (m, 1H), 4.72 (t, J=11.8 Hz, 1H), 5.23 (d, J=11.7 Hz, 1H), 5.36 (d, J=8.5 Hz, 1H), 5.71 (d, J=8.8 Hz, 1H)

¹³C-NMR (125 MHZ, DMSO-d6) δ: 15.0, 18.5, 22.7, 27.8, 29.0, 29.1, 31.5, 34.0, 37.0, 55.3, 55.58, 55.65, 59.9, 177.2, 177.5

MS (FAB): m/z 492 (M+H⁺)

From the above results, it was identified that this compound had the chemical structure which was represented by the (compound 5).

[Chemical Formula 38]

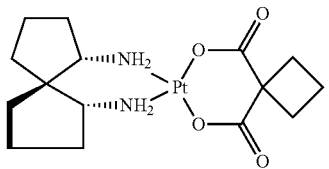

(Compound 5)

Embodiment 7

The test solution was prepared by dissolving the (compound 1) into the dimethylsulfoxide (UMBO) with the concentration of 8 mg/ml.

The test was performed by using the U937 (human lymphoma cell) as the cancer cell and using the HEK293 (human fetus kidney cell) as the normal cell.

These cells were suspended in the each culture medium that the serum of 10% was added, and were dispensed in 96-well plate. And then, these were cultured in 5% CO₂ at 37 degrees centigrade during a night. Next day, the test solution was prepared in the culture medium to the various concentrations (0, 4, 8, 16 μg/ml), and was dispensed into the plate that the cells were set preliminarily. And further, these were cultured in 5% CO₂ at 37 degrees centigrade for three days.

The cell proliferation after the medicine addition was measured on the 3rd day from the 1st day after the medicine addition by the NTS method (Kit for cell proliferation test manufactured by Promega Company).

The inhibition rate (%) of the cell proliferation was obtained from the measured MTS value by the following formula.

Inhibition rate(%)=(1-MTS value of medicine addition group/MTS value of medicine non-addition group)×100

Because the value which was obtained by the above-mentioned formula represents the inhibition rate of the cell proliferation, the higher the numerionl value is, the higher the medicine effect is. It is deemed that the one whose value is 50% or more has the medicine effect. The result is represented below.

The X axis of the graph which is represented in FIG. 1 represents the days after the medicine addition, and the Y axis represents the inhibition rate (%) of the cell proliferation which is obtained from the formula. Further, each concentration (4, 8, 16 μg/ml) is represented on the same graph.

TABLE 1

Inhibition rate of cell proliferation for 1st to 3rd day from medicine addition (%)

| Concentration of medicinal solution (μg/ml) | Effect of medicine of compound 1 to U937 | | | Effect of medicine of compound 1 to HEK293 | | | Effect of oxaliplatin to U937 | | |
| --- | --- | --- | --- | --- | --- | --- | --- | --- | --- |
| | 1st day | 2nd day | 3rd day | 1st day | 2nd day | 3rd day | 1st day | 2nd day | 3rd day |
| 0 | 0 | 0 | 0 | 0 | 0 | 0 | 0 | 0 | 0 |
| 4 | 32 | 97 | 99 | 6 | 14 | −27 | −5 | −26 | 12 |
| 8 | 77 | 98 | 100 | 19 | 43 | 19 | −1 | −5 | 37 |
| 16 | 91 | 98 | 99 | 54 | 84 | 84 | 0 | 30 | 73 |

From the above-mentioned Table 1, the remarkable medicine effect was recognized in the cancer cell (U937). As the result that the above-mentioned similar test was performed about the oxaliplatin, although the medicine effect was also recognized in U937, it became clear that the medicine effect of the (compound 1) was stronger.

Embodiment 8

Respectively, the S medicine test solution was prepared by dissolving the ((S,S,S) cis,cis-spiro[4,4]nonane-1,6-diamine)oxalatoplatinum(II) complex (compound 2; hereinafter, it is described as S medicine) into the dimethylsulfoxide (DMSO) with the concentration of 10 mg/ml and the R medicine test solution was prepared by dissolving the ((R,R,R)cis, cis-spiro[4,4]nonane-1,6-diamine) oxalatoplatinum(II) complex (compound 3; hereinafter, it is described as R medicine) into the dimethylsulfoxide (DMSO) with the concentration of 10 mg/ml.

The test was performed by using A549 (human lung cancer cell), LU65A (human lung cancer cell), RERF-LC-MA (human lung cancer cell), LU99 (human lung cancer cell), H460 (human lung cancer cell), HCT116 (human colon cancer cell), HT-29 (human colon cancer cell), MKN-45 (human gastric cancer cell), MKN-1 (human gastric cancer cell), U937 (human lymphoma cell), KP-1N (human pancreas cancer cell) and B2452 (human mesotheliama cell) as the cancer cell.

These cells were suspended in the each culture medium that the serum of 10% was added, and were dispensed in 96-well plate. And then, these were cultured in 5% $CO_2$ at 37 degrees centigrade during a night. Next day, the S medicine test solution and the R medicine test solution were prepared in the culture medium to the various concentrations (5, 10, 20 µg/ml), and were dispensed into the plates that the cells were set preliminarily. And further, these were cultured in 5% $CO_2$ at 37 degrees centigrade for three days.

The cell proliferation after the medicine addition was measured on the 3rd day from the 1st day after the medicine addition by the MTS method (kit for cell proliferation test manufactured by Promega Company).

The inhibition rate (%) of the cell proliferation was obtained from the measured MTS value by the following formula.

Inhibition rate(%)=(1-MTS value of medicine addition group/MTS value of medicine non-addition group)×100

Because the value which was obtained by the above-mentioned formula represents the inhibition rate of the cell proliferation, the higher the numerical value is, the higher the medicine effect is. It is desired that the one whose value is 50% or more has the medicine effect. The result is represented below.

Figure 2:
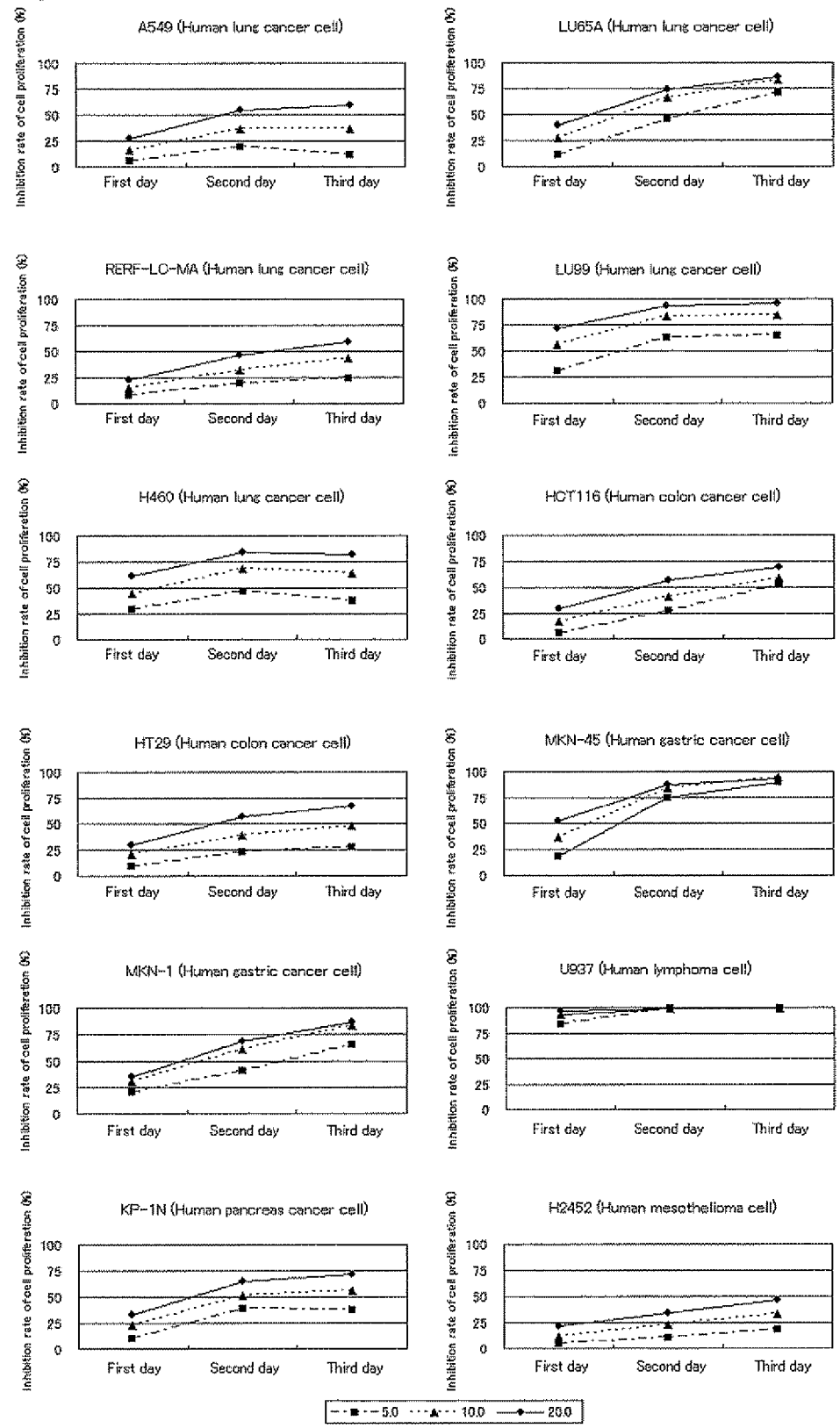
FIG. 2 The graph representing the inhibition rate (%) of the cell proliferation when making the (compound 2) of this invention act on the various cancer cells.
Figure 3:
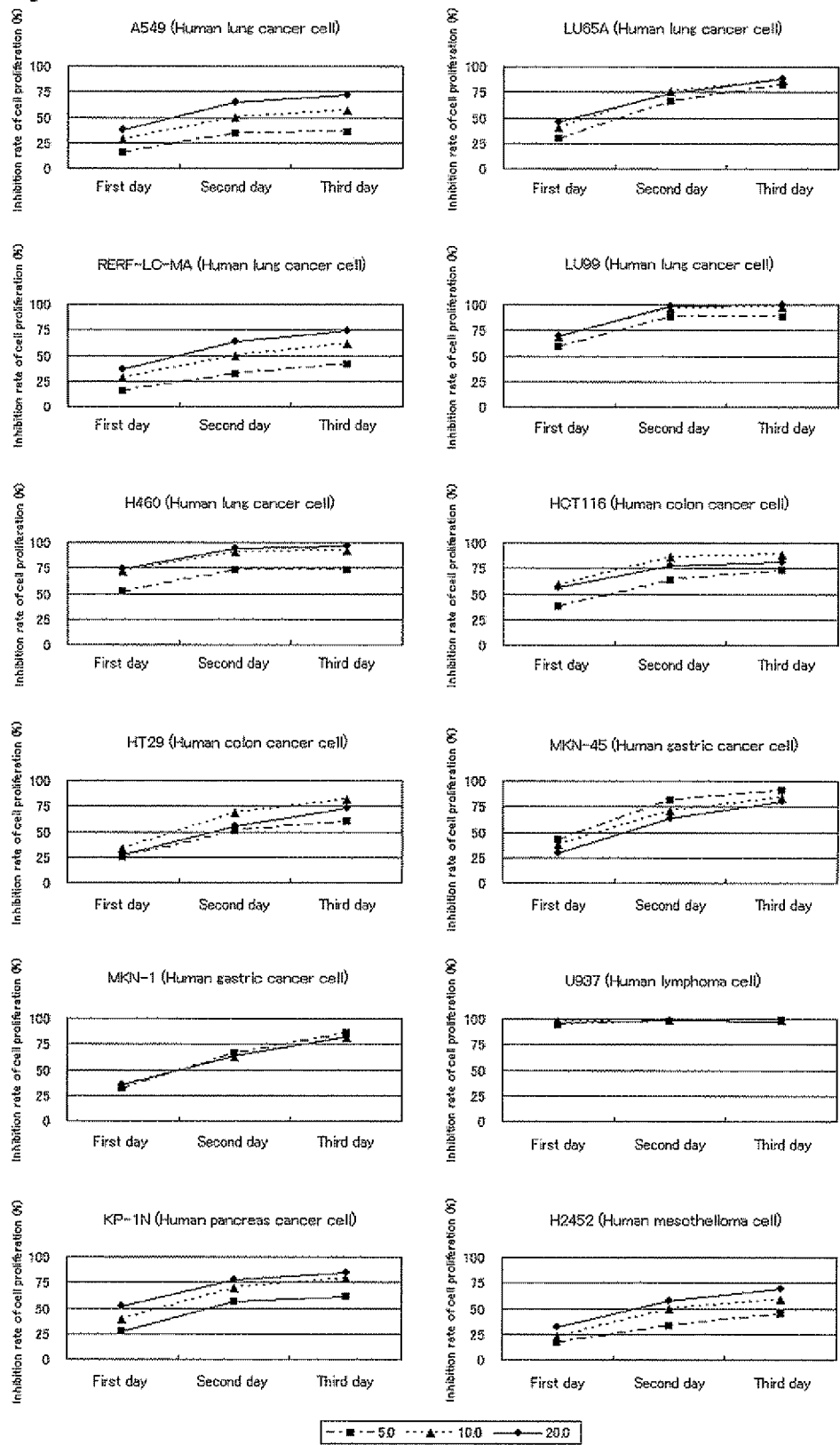
FIG. 3 The graph representing the inhibition rate (%) of the cell proliferation when making the (compound 3) of this invention act on the various cancer cells.

The X axis of the graph which is represented in FIG. 2 and FIG. 3 represents the days after the medicine addition, and the Y axis represents the inhibition rate (%) of the cell proliferation which is obtained from the formula. Further, each concentration (5, 10, 2 µg/ml) is represented on the same graph.

TABLE 2

Inhibition rate of cell proliferation after 3 days from medicine addition (%)

| | Concentration of medicinal solution (µg/ml) | | | | | | | | |
|---|---|---|---|---|---|---|---|---|---|
| | S medicine | | | R medicine | | | Oxaliplatin | | |
| | 5 | 10 | 20 | 5 | 10 | 20 | 5 | 10 | 20 |
| A549 | X | ○ | ◎ | Δ | ○ | ○ | — | X | Δ |
| LU65A | ○ | ◎ | ◎ | ◎ | ◎ | ◎ | — | Δ | ○ |
| RERF-LC-MA | X | Δ | ○ | Δ | ○ | ○ | — | X | X |
| LU99 | ○ | ◎ | ◎ | ◎ | ◎ | ◎ | — | ○ | ○ |
| H460 | Δ | ○ | ◎ | ○ | ◎ | ◎ | — | Δ | Δ |
| HCT116 | ○ | ○ | ○ | ○ | ◎ | ◎ | — | ○ | ○ |
| HT-29 | Δ | Δ | ○ | ○ | ○ | ◎ | — | Δ | Δ |
| MKN-45 | ◎ | ◎ | ◎ | ◎ | ◎ | ◎ | — | ◎ | ◎ |
| MKN-1 | ○ | ◎ | ◎ | ◎ | ◎ | ◎ | — | ○ | ◎ |
| U937 | ◎ | ◎ | ◎ | ◎ | ◎ | ◎ | — | ◎ | ◎ |
| KP-1N | Δ | ○ | ◎ | ○ | ◎ | ◎ | — | Δ | ○ |
| H2452 | X | Δ | Δ | Δ | ○ | ○ | — | Δ | Δ |

X: 0~25%
Δ: 26~50%
○: 51~75%
◎: 76~100%
—: Non-measurement

Concerning the S medicine, the inhibition rate of the cell proliferation was 50% or more in the all cells except the H2452 cell (human mesothelicana cell). Concerning the R medicine, the inhibition rate of the cell proliferation was 50% or more in the all cells.

From, the above results, the S medicine and the R medicine represent the medicine effect for the many tumor cells, and the R medicine is higher in the effect. And, the S medicine and the R medicine represent the high medicine effect compared with the oxaliplatin which is the conventional antitumor therapeutic agent.

INDUSTRIAL APPLICABILITY

As described above, the platinum complex of this invention has the strong antitumor activity, and is efficacious as the therapeutic agent for the malignant tumor.

The invention claimed is:
1. A platinum complex, characterized by comprising:
   a spiro[4,4]nonane-1,6-diamineplatinum(II) complex represented by a following general formula (A):

(A)

(in the formula, X and Y are same or different, and X and Y represent halogen atoms respectively, or X and Y cooperatively represent the divalent residue which is described by a formula (Z));

(Z)

(in the formula, R represents a single bond or represents a straight-chain or branched-chain divalent hydrocarbon residue whose number of carbon atom is 1-6, the hydrocarbon residue may have an unsaturated bond, and the hydrocarbon residue may form a spiro structure).

2. The platinum complex, according to claim 1, characterized by comprising:
a (S,S,S)-cis,cis-spiro[4,4]nonane-1,6-diamineplatinum(II) complex represented by a following general formula (B):

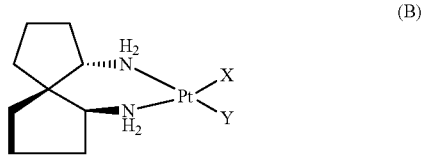

(B)

(in the formula, X and Y are same or different, and X and Y represent halogen atoms respectively, or X and Y cooperatively represent the divalent residue which is described by the formula (Z)):

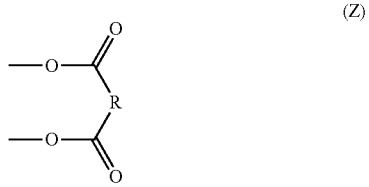

(Z)

(in the formula, R represents the single bond or represents the straight-chain or branched-chain divalent hydrocarbon residue whose number of carbon atom is 1-6, the hydrocarbon residue may have the unsaturated bond, and the hydrocarbon residue may form the spiro structure).

3. The platinum complex, according to claim 1, characterized by comprising:
a (R,R,R)-cis,cis-spiro[4,4]nonane-1,6-diamineplatinum(II) complex represented by an undermentioned general formula (C):

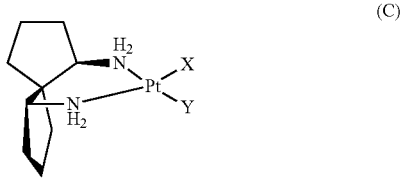

(C)

(in the formula, X and Y are same or different, and X and Y represent halogen atoms respectively, or X and Y cooperatively represent the divalent residue which is described by the formula (Z)):

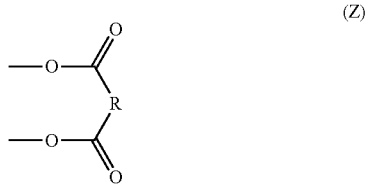

(Z)

(in the formula, R represents the single bond or represents the straight-chain or branched-chain divalent hydrocarbon residue whose number of carbon atom is 1-6, said hydrocarbon residue may have the unsaturated bond, and said hydrocarbon residue may form the spiro structure).

4. The platinum complex, according to claim 1, characterized by comprising:
a (spiro[4,4]nonane-1,6-diamine)dicaboxylatoplatinum(II) complex represented by a following general formula (D):

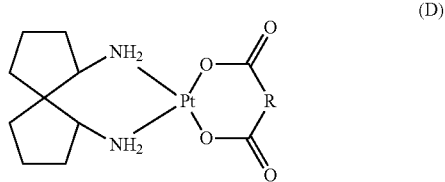

(D)

(in the formula, R represents the single bond or represents the straight-chain or branched-chain divalent hydrocarbon residue whose number of carbon atom is 1-6, the hydrocarbon residue may have the unsaturated bond, and the hydrocarbon residue may form the Spiro structure).

5. The platinum complex, according to claim 2, characterized by comprising:
a ((S,S,S)-cis,cis-spiro[4,4]nonane-1,6-diamine)dicarboxylatoplatinum(II) complex represented by a following general formula (E):

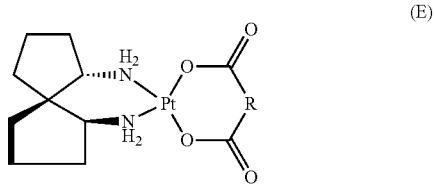

(E)

(in the formula, R represents the single bond or represents the straight-chain or branched-chain divalent hydrocarbon residue whose number of carbon atom is 1-6, the hydrocarbon residue may have the unsaturated bond, and the hydrocarbon residue may form the Spiro structure).

6. The platinum complex, according to claim 3, characterized by comprising:
a ((R,R,R)-cis,cis-spiro[4,4]nonane-1,6-diamine)dicarboxylatoplatinum(II) complex represented by a following general formula (F):

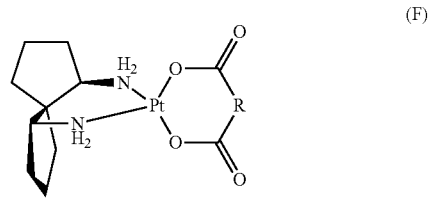

(F)

(in the formula, R represents the single bond or represents the straight-chain or branched-chain divalent hydrocarbon residue whose number of carbon atom is 1-6, the hydrocarbon residue may have the unsaturated bond, and the hydrocarbon residue may form the Spiro structure).

7. The platinum complex, according to claim 1, characterized by comprising:
   a (cis,cis-spiro[4,4]nonane-1,6-diamine)oxalatoplatinum(II) complex represented by a following formula (G):

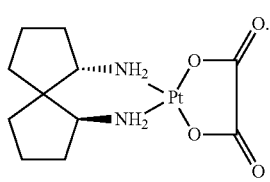
(G)

8. The platinum complex, according to claim 5, characterized by comprising:
   a ((S,S,S)-cis,cis-spiro[4,4]nonane-1,6-diamine)oxalatoplatinum(II) complex represented by a following formula (H):

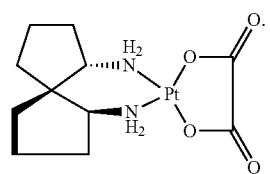
(H)

9. The platinum complex, according to claim 6, characterized by comprising:
   a ((R,R,R)-cis,cis-spiro[4,4]nonane-1,6-diamine)oxalatoplatinum(II) complex represented by a following formula (J):

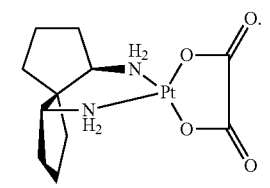
(J)

10. The platinum complex, according to claim 1, characterized by comprising:
    a (cis,cis-spiro[4,4]nonane-1,6-diamine)cyclobutanedicarboxylatoplatinum(II) complex represented by a following formula (K):

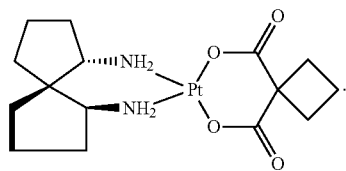
(K)

11. The platinum complex, according to claim 1, characterized by comprising:
    a (cis,trans-spiro[4,4]nonane-1,6-diamine)cyclobutanedicarboxylatoplatinum(II) complex represented by a following formula (L):

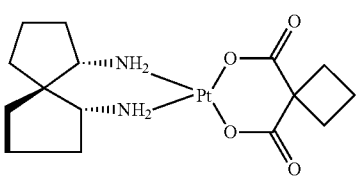
(L)

12. A pharmaceutical composition, characterized in that:
    a platinum complex described in claim 1 is contained as an active ingredient.

13. A therapeutic agent for a malignant tumor, characterized in that
    a platinum complex described in claim 1 is contained as an active ingredient.

14. A pharmaceutical composition, characterized by comprising:
    a therapeutic agent for a malignant tumor of claim 13.

15. A pharmaceutical composition, characterized by comprising:
    a therapeutic agent for a nonsolid malignant tumor of claim 13.

* * * * *